United States Patent
Grichnik et al.

(10) Patent No.: US 8,260,636 B2
(45) Date of Patent: Sep. 4, 2012

(54) METHOD AND SYSTEM FOR PRIORITIZING COMMUNICATION OF A HEALTH RISK

(75) Inventors: Anthony J. Grichnik, Peoria, IL (US); Michael L. Taylor, Morton, IL (US)

(73) Assignee: Caterpillar Inc., Peoria, IL (US)

( * ) Notice: Subject to any disclaimer, the term of this patent is extended or adjusted under 35 U.S.C. 154(b) by 934 days.

(21) Appl. No.: 11/896,385

(22) Filed: Aug. 31, 2007

(65) Prior Publication Data

US 2009/0062621 A1    Mar. 5, 2009

(51) Int. Cl.
*G06Q 50/00* (2012.01)

(52) U.S. Cl. ......... 705/3

(58) Field of Classification Search ........ 705/2–3
See application file for complete search history.

(56) References Cited

U.S. PATENT DOCUMENTS

| | | | |
|---|---|---|---|
| 6,240,343 B1 | 5/2001 | Sarangapani | |
| 7,181,375 B2 | 2/2007 | Rao et al. | |
| 7,213,007 B2 | 5/2007 | Grichnik | |
| 7,226,792 B2 | 6/2007 | Roberts et al. | |
| 2002/0002472 A1 | 1/2002 | Abraham-Fuchs | |
| 2002/0082869 A1 | 6/2002 | Anderson | |
| 2002/0194032 A1 | 12/2002 | Mankopf et al. | |
| 2003/0097279 A1* | 5/2003 | deLusignan et al. ........... 705/2 |
| 2003/0119194 A1* | 6/2003 | Otvos ........... 436/71 |
| 2003/0135391 A1 | 7/2003 | Edmundson et al. | |
| 2003/0204412 A1 | 10/2003 | Brier | |
| 2004/0015337 A1 | 1/2004 | Thomas et al. | |
| 2004/0139041 A1 | 7/2004 | Grichnik | |
| 2004/0225200 A1 | 11/2004 | Edmundson et al. | |
| 2004/0249672 A1 | 12/2004 | Bocionek et al. | |
| 2005/0009035 A1* | 1/2005 | Caspi et al. ........... 435/6 |
| 2005/0060193 A1* | 3/2005 | Lancaster et al. ........... 705/2 |
| 2005/0137905 A1 | 6/2005 | Haas et al. | |
| 2005/0154616 A1 | 7/2005 | Iliff | |
| 2005/0228692 A1* | 10/2005 | Hodgdon ........... 705/2 |
| 2006/0047538 A1 | 3/2006 | Condurso et al. | |
| 2006/0178837 A1 | 8/2006 | Gill-Garrison et al. | |
| 2006/0200368 A1 | 9/2006 | Casey | |
| 2006/0224416 A1 | 10/2006 | Lloyd et al. | |
| 2006/0229917 A1 | 10/2006 | Simske et al. | |
| 2007/0027636 A1 | 2/2007 | Rabinowitz | |
| 2007/0027723 A1 | 2/2007 | Bardy | |
| 2007/0050214 A1 | 3/2007 | Hawks et al. | |
| 2007/0050215 A1 | 3/2007 | Kil et al. | |
| 2007/0073558 A1 | 3/2007 | Hall et al. | |
| 2007/0094048 A1 | 4/2007 | Grichnik | |
| 2007/0179349 A1 | 8/2007 | Hoyme et al. | |
| 2007/0179351 A1 | 8/2007 | Kil et al. | |
| 2007/0179769 A1 | 8/2007 | Grichnik | |

* cited by examiner

*Primary Examiner* — Gerald J. O'Connor
*Assistant Examiner* — Sind Phongsvirajati
(74) *Attorney, Agent, or Firm* — Finnegan, Henderson, Farabow, Garrett & Dunner LLP

(57) ABSTRACT

System and methods are provided for prioritizing communication of a health risk. The method may include obtaining health information for individuals and determining, based on the health information, a risk of each individual contracting each of plurality of diseases. The method may also include calculating, based on the risks, an average risk of each individual contracting the diseases and selecting a subset of the individuals based on the average risks. Further, the method may include calculating an improved risk by making lifestyle changes for the subset of the individuals and communicating the health risks and the lifestyle changes to individuals in the subset based on the amount of improved risk.

20 Claims, 3 Drawing Sheets

METHOD AND SYSTEM FOR PRIORITIZING COMMUNICATION OF A HEALTH RISK

TECHNICAL FIELD

This disclosure relates generally to health care, and, more particularly, to methods and systems for prioritizing communication of a health risk.

BACKGROUND

Advertisements often communicate health risks to the general public. For example, an advertisement may indicate that losing weight can reduce an individual's risk of contracting heart disease. However, advertisements that are directed to the general public are unlikely to cause individuals to take action. For example, advertisements may not be relevant to an individual, such as when an individual has a healthy weight. Others who could reduce their risk of contracting heart disease may ignore the advertisement because it is directed to the general public. As a result, the health promotion program may be ineffective.

One solution to this problem is directly contacting individuals by a physician to communicate the risk of contracting a disease and provide personalized recommendations. For example, if a physician tells an individual that losing weight may reduce the risk of contracting heart disease, the individual may be more likely to lose weight compared to when the individual sees an advertisement. However, many individuals do not regularly see physicians or they may visit a physician too late to prevent contracting a disease. Moreover, personal contact by a physician may be too expensive to effectively administer for all diseases and for each individual.

One tool that has been developed for predicting and minimizing future behavioral health-related hospital admissions is U.S. Patent Application Publication No. 2006/0224416 A1 (the '416 publication). The '416 publication identifies individuals at high risk of hospital admission. If the individual is at high risk, the '416 publication discloses intervening to modify the risk factors that place the individual at high risk.

Although the tool of the '416 publication identifies individuals at high risk for a specific disorder based on medical history, the '416 publication does not allow identifying a high risk for a plurality of diseases. The '416 publication also does not analyze the amount of improvement that an individual can obtain by making lifestyle changes prior to communicating with the individual. Accordingly, the '416 publication does not prioritize communication to individuals based on the level of risk or the amount of potential improvement to risk.

The present disclosure is directed to overcoming one or more of the problems set forth above.

SUMMARY OF THE INVENTION

In accordance with one aspect, the present disclosure is directed toward a computer-readable medium comprising instructions which, when executed by a processor, perform a method for prioritizing communication of a health risk. The method may include obtaining health information for individuals and determining, based on the health information, a risk of each individual contracting each of plurality of diseases. The method may also include calculating, based on the risks, an average risk of each individual contracting the diseases and selecting a subset of the individuals based on the average risks. Further, the method may include calculating an improved risk by making lifestyle changes for the subset of the individuals and communicating the health risks and the lifestyle changes to individuals in the subset based on the amount of improved risk.

According to another aspect, the present disclosure is directed toward a method for prioritizing communication of a health risk. The method may include obtaining health information for individuals and determining, based on the health information, a risk of each individual contracting each of plurality of diseases. The method may also include calculating, based on the risks, an average risk of each individual contracting the diseases and selecting a subset of the individuals based on the average risks. Further, the method may include calculating an improved risk by making lifestyle changes for the subset of the individuals and communicating the health risks and the lifestyle changes to individuals in the subset based on the amount of improved risk.

According to another aspect, the present disclosure is directed to a computer system including memory, at least one input device, and a central processing unit in communication with the memory and the at least one input device. The central processing unit may obtain health information for individuals and determine, based on the health information, a risk of each individual contracting each of plurality of diseases. The central processing unit may also calculate, based on the risks, an average risk of each individual contracting the diseases and select a subset of the individuals based on the average risks. Further, the central processing unit may calculate an improved risk by making lifestyle changes for the subset of the individuals and communicate the health risks and the lifestyle changes to individuals in the subset based on the amount of improved risk.

DETAILED DESCRIPTION

Reference will now be made in detail to exemplary embodiments, which are illustrated in the accompanying drawings. Wherever possible, the same reference numbers will be used throughout the drawings to refer to the same or like parts.

Figure 1:
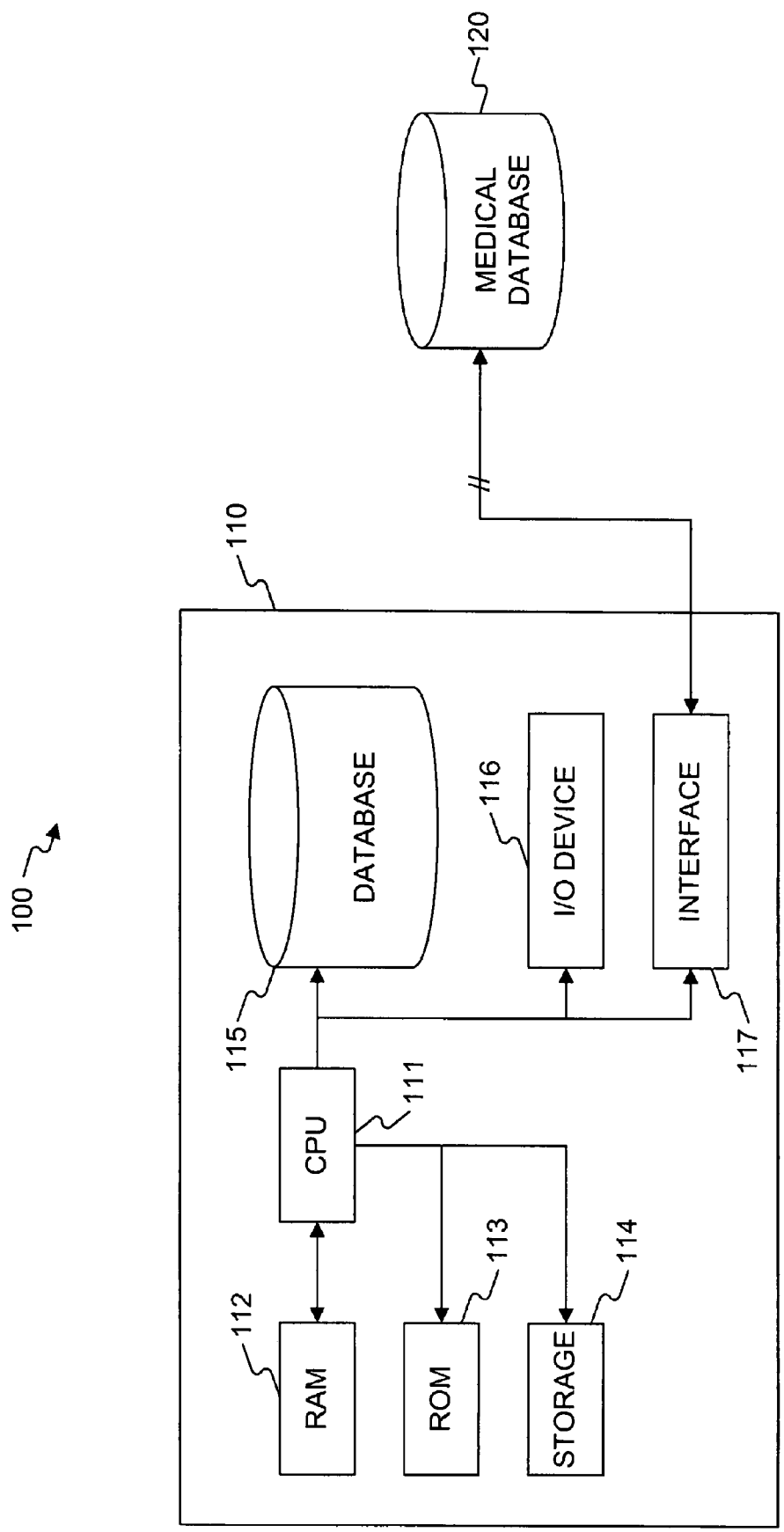
FIG. 1 is a block illustration of an exemplary disclosed system for prioritizing communication of a health risk.

FIG. 1 provides a block diagram illustrating an exemplary environment 100 for prioritizing communication of a health risk. Environment 100 may include a system 110 and a medical database 120. System 110 may be, for example, a general purpose personal computer or a server. Although illustrated as a single system 110, a plurality of systems 110 may connect to other systems, to a centralized server, or to a plurality of distributed servers using, for example, wired or wireless communication.

System 110 may include any type of processor-based system on which processes and methods consistent with the disclosed embodiments may be implemented. For example, as illustrated in FIG. 1, system 110 may include one or more hardware and/or software components configured to execute software programs. System 110 may include one or more hardware components such as a central processing unit (CPU) 111, a random access memory (RAM) module 112, a read-only memory (ROM) module 113, a storage 114, a database 115, one or more input/output (I/O) devices 116, and an interface 117. System 110 may include one or more software components such as a computer-readable medium including computer-executable instructions for performing methods consistent with certain disclosed embodiments. One or more of the hardware components listed above may be implemented using software. For example, storage 114 may include a software partition associated with one or more other hardware components of system 110. System 110 may include additional, fewer, and/or different components than those listed above, as the components listed above are exemplary only and not intended to be limiting.

CPU 111 may include one or more processors, each configured to execute instructions and process data to perform one or more functions associated with system 110. As illustrated in FIG. 1, CPU 111 may be communicatively coupled to RAM 112, ROM 113, storage 114, database 115, I/O devices 116, and interface 117. CPU 111 may execute sequences of computer program instructions to perform various processes, which will be described in detail below. The computer program instructions may be loaded into RAM for execution by CPU 111.

RAM 112 and ROM 113 may each include one or more devices for storing information associated with an operation of system 110 and CPU 111. RAM 112 may include a memory device for storing data associated with one or more operations of CPU 111. For example, ROM 113 may load instructions into RAM 112 for execution by CPU 111. ROM 113 may include a memory device configured to access and store information associated with system 110, including information for prioritizing communication of a health risk to an individual.

Storage 114 may include any type of mass storage device configured to store information that CPU 111 may need to perform processes consistent with the disclosed embodiments. For example, storage 114 may include one or more magnetic and/or optical disk devices, such as hard drives, CD-ROMs, DVD-ROMs, or any other type of mass media device.

Database 115 may include one or more software and/or hardware components that cooperate to store, organize, sort, filter, and/or arrange data used by system 110 and CPU 111. Database 115 may store data collected by system 110 to monitor health, identify health risks, prioritize communication of health risks, and communicate health risks to individuals.

I/O device 116 may include one or more components configured to communicate information to a user associated with system 110. For example, I/O devices may include a console with an integrated keyboard and mouse to allow a user to input parameters associated with system 110. I/O device 116 may also include a display, such as a monitor, including a graphical user interface (GUI) for outputting information. I/O devices 116 may also include peripheral devices such as, for example, a printer for printing information and reports associated with system 110, a user-accessible disk drive (e.g., a USB port, a floppy, CD-ROM, or DVD-ROM drive, etc.) to allow a user to input data stored on a portable media device, a microphone, a speaker system, or any other suitable type of interface device.

The results of received data may be provided as an output from system 110 to I/O device 116 for printed display, viewing, and/or further communication to other system devices. Output from system 110 may also be provided to database 115 and to medical database 120.

Interface 117 may include one or more components configured to transmit and receive data via a communication network, such as the Internet, a local area network, a workstation peer-to-peer network, a direct link network, a wireless network, or any other suitable communication platform. In this manner, system 110 may communicate with other network devices, such as dictionary database 120, through the use of a network architecture (not shown). In such an embodiment, the network architecture may include, alone or in any suitable combination, a telephone-based network (such as a PBX or POTS), a local area network (LAN), a wide area network (WAN), a dedicated intranet, and/or the Internet. Further, the network architecture may include any suitable combination of wired and/or wireless components and systems. For example, interface 117 may include one or more modulators, demodulators, multiplexers, demultiplexers, network communication devices, wireless devices, antennas, modems, and any other type of device configured to enable data communication via a communication network.

Medical database 120 may store information regarding individuals that may be useful in identifying potential health risks. Exemplary information includes an individual's height, weight, blood pressure, resting pulse, x-ray results, lab test results, health history, name, ethnicity, contact information (e.g., mailing address, e-mail address, phone numbers), the individual's insurance company and doctors, and any other information that may be useful for predicting a health risk. Medical database 120 may also store one or more algorithms for predicting whether an individual will contract a disease and determining whether the individual may reduce their risk of contracting a disease by making lifestyle changes. Although several examples of health information have been provided, many other types of health information may be stored in medical database 120 as needed to predict, identify, and treat a variety of diseases.

Although not illustrated, one or more servers may contain medical database 120. A server may collect data from a plurality of systems 110 to provide a central repository for identifying, prioritizing, and communicating health risks to individuals. Moreover, medical database 120 may include one or more databases that are in the same or different location. Examples of identifying and prioritizing communication of a health risk will be described below with reference to FIG. 3.

Those skilled in the art will appreciate that all or part of systems and methods consistent with the present disclosure may be stored on or read from other computer-readable media. Environment 100 may include a computer-readable medium having stored thereon machine executable instructions for performing, among other things, the methods disclosed herein. Exemplary computer readable media may include secondary storage devices, like hard disks, floppy disks, and CD-ROM; or other forms of computer-readable memory, such as read-only memory (ROM) 113 or random-access memory (RAM) 112. Such computer-readable media may be embodied by one or more components of environment 100, such as CPU 111, storage 1113, database 115, medical database 120.

Furthermore, one skilled in the art will also realize that the processes illustrated in this description may be implemented in a variety of ways and include other modules, programs, applications, scripts, processes, threads, or code sections that may all functionally interrelate with each other to provide the functionality described above for each module, script, and daemon. For example, these programs modules may be implemented using commercially available software tools, using custom object-oriented code written in the C++ programming language, using applets written in the Java programming language, or may be implemented with discrete electrical components or as one or more hardwired application specific integrated circuits (ASIC) that are custom designed for this purpose.

The described implementation may include a particular network configuration, but embodiments of the present disclosure may be implemented in a variety of data communication network environments using software, hardware, or a combination of hardware and software to provide the processing functions.

Processes and methods consistent with the disclosed embodiments may prioritize communication of health risks. System 110 may identify individuals who are likely to contract a disease, determine which individuals are most likely to reduce their risk of contracting a disease by making lifestyle changes, and prioritize communication of health risks. As a result, individuals who are most likely to reduce their chance of contracting a disease may be notified prior to disease onset, allowing the individual to make preventative changes, reduce their risk of contracting a disease, and reduce health care costs.

Exemplary processes and methods consistent with the invention will now be described with reference to FIGS. 2 and 3.

Industrial Applicability

The disclosed methods and systems provide a desired solution for prioritizing communication of health risks. Individuals can track the likelihood of contracting a disease and make lifestyle changes while the likelihood of preventing or effectively treating a disease is great. Companies can track the health of their employees and notify them of health risks, reducing the cost of health care and allowing employees to continue working. Accordingly, environment 100 may allow detection and communication of health risks to increase the possibility of survival from a disease and to reduce health care costs.

Figure 2:
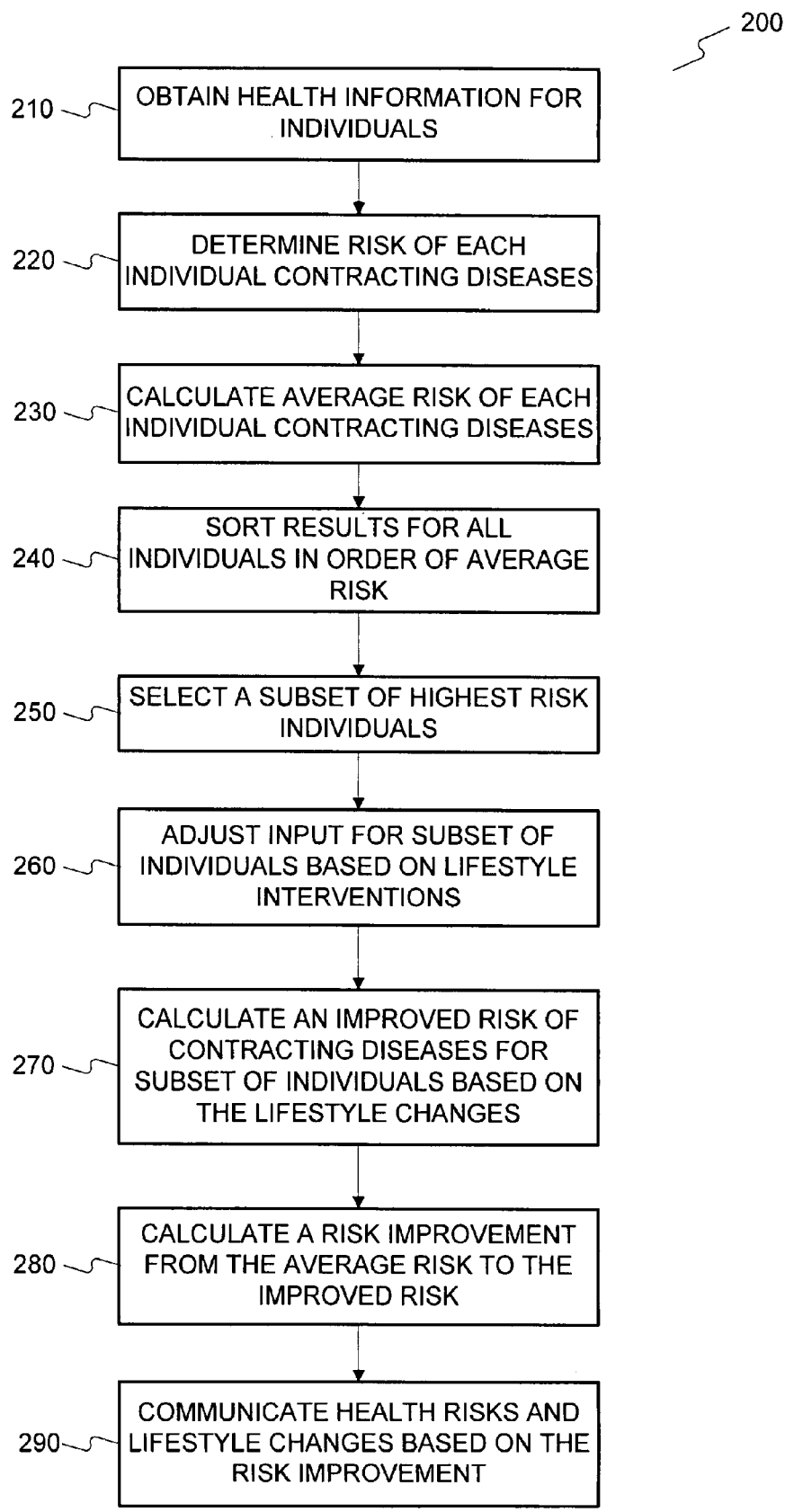
FIG. 2 is a flowchart illustration of an exemplary disclosed method for prioritizing communication of a health risk.

FIG. 2 is a flowchart illustration of an exemplary disclosed method 200 for prioritizing communication of a health risk. System 110 may perform method 200 periodically (e.g., every month), on demand, continuously, or at a triggering event, such as when a patient visits a doctor. System 110 may be run by, for example, a company or a health insurance company to prioritize communication of health risks to employees and insured individuals. Doctors and medical students may also use method 200 to study changing health risks for a sample population. System 110 may predict the risk of any disease or any combination of diseases, such as various forms of cancer, heart disease, diabetes, cardiovascular disease, and other diseases.

Method 200 may begin with system 110 obtaining health information for individuals (Step 210). System 110 may gather health information from, for example, doctors that individuals visit, insurance companies that individuals use, individuals through the use of one or more web-based forms, a company upon initial hiring of individuals (e.g., performing a physical or drug test), or any other source. System 110 may store the health information in, for example, database 115 and medical database 120. Individuals may also identify the amount of health information that system 110 can collect, allowing individuals to maintain their privacy.

Next, system 110 may determine a risk of each individual contracting a disease (Step 220). System 110 may analyze the risk of all diseases or only those diseases that individuals are likely to contract based on the collected health information. System 110 may determine a risk of each individual contracting each selected disease using one or more developed models. For example, system 110 may predict an individual's risk of heart disease or stroke based on the Framingham Heart Study. Examples of health information for the Framingham Heart Study may include an individual's age, gender, systolic blood pressure, whether the individual smokes, whether the individual has any significant heart murmurs, and other health history, such as prior heart failures. Other forecasting models may also be used, such as an autoregressive integrated moving average model disclosed in U.S. Pat. No. 7,213,007 or the method for forecasting using a genetic algorithm disclosed in U.S. Patent Application Publication No. 2004/0139041. Moreover, multiple models may be used, and system 110 may normalize scores of the models to a standard scale, such as 0 to 100, with 100 indicating that an individual has the disease.

Next, system 110 may calculate an average risk of each individual contracting selected diseases. Assume that system 110 monitors individuals for cardiovascular disease and diabetes. If system 110 determines in Step 220 that an individual has a scaled risk of contracting cardiovascular disease of 70 and a scaled risk of contracting diabetes of 30, the individual's average risk of contracting cardiovascular disease and diabetes is 50. System 110 may select diseases to average risks together based on, for example, medical data that indicates which diseases are likely to share common traits, which diseases can be prevented using similar treatments, which diseases an individual has a highest possibility of preventing, which diseases can be prevented with minimal cost or inconvenience to an individual or a company, and any other criteria. Moreover, the average risk may be weighted more heavily based on any of the above factors. For example, if a disease is more likely to lead to severe consequences, the average risk may weight it more heavily. Although an example of averaging two diseases has been described, any number of diseases may be averaged.

System 110 may then sort the results for all individuals in order of average risk (Step 240). Continuing with the example above, assume that a company monitors employees for a risk of contracting cardiovascular disease and diabetes. The company may have tens of thousands of employees. System 110 may also combine all of the averaged risks for each individual into a sorted listed, with individuals that have a highest average risk at the top of the list and individuals having a low averaged risk at the bottom.

Next, system 110 may select a subset of highest risk individuals (Step 250). For example, system 110 may select the top 1% of individuals sampled. If a company has 150,000 employees, the 1,500 individuals with the highest average risk may be selected for inclusion in the subset. The percentage or number of individuals to select for inclusion in the subset may be any suitable amount that system 110 can handle. For example, a small company having several hundred employees may be able to monitor all of their employees, whereas a larger company may have to create a smaller subset (e.g., 20%) to ensure that health risks can be properly addressed. Moreover, system 110 may determine the size of the subset in a manner that ensures individuals will not be unnecessarily informed of a minimal health risk. System 110 may also determine the size of the subset based on the combined average risk. For example, all individuals having a combined average risk of contracting diseases above 50 may be included in the subset. Further, system 110 may determine the size of the subset based by identifying individuals who can achieve a defined reduction in average risk by implementing a defined number of lifestyle changes. System 110 may select the individuals to include in the subset from the sorted list created in Step 240.

Next, system 110 may adjust input for the subset of individuals based on preventative lifestyle interventions (Step 260). Exemplary lifestyle interventions include losing weight, reducing cholesterol, maintaining a healthy blood pressure, eating more fruits and vegetables, stopping smoking, exercising, eating fewer saturated fats, and eating more whole grain, although any other lifestyle intervention may be performed based on the disease and individual. For example, if an individual smokes, has high cholesterol, and has a high risk of contracting cardiovascular disease, recommended lifestyle interventions may include stopping smoking and cholesterol management through a revised diet. System 110 may change input to include lifestyle changes for each individual and the disease based on the health information for each individual. For example, system 110 may not change the input to reflect a different cholesterol if the individual already has healthy cholesterol levels.

Further, system 110 may calculate an improved risk of contracting diseases for the subset of individuals based on the lifestyle changes (Step 270). System 110 may therefore determine how making lifestyle changes would affect the risk of each individual contracting the diseases. For example, if an individual lost 40 pounds, system 110 may use the reduced weight to re-calculate the individual's risk for contracting diseases. System 110 may calculate one or more improved risks for each disease based on one or more lifestyle changes.

System 110 may then calculate a risk improvement between the average risk and the improved risk (Step 280). Calculating the risk improvement may allow system 110 to identify individuals who may greatly reduce their risk for contracting diseases while making minimal lifestyle changes. Individuals who may require multiple lifestyle changes may be unlikely to make the recommended lifestyle changes, and their risk for contracting a disease therefore may remain unchanged. However, individuals who can make fewer lifestyle changes, such as only eating more whole grain foods, while obtaining a large reduction in risk for contracting a disease (e.g., a 30% reduction in risk for contracting diabetes or the combination of diabetes and cardiovascular disease) may be more likely to make the recommended lifestyle changes. System 110 may divide the subset of individuals into one or more groups based on the amount of risk improvement.

Next, system 110 may communicate health risks and recommended lifestyle changes to the subset of individuals based on the risk improvement (Step 290). System 110 may use differing forms of communication for the groups of individuals in the subset depending on, for example, the number of lifestyle interventions required, the seriousness of the disease, the likelihood of contracting the disease or diseases, the amount of reduction in risk possible by performing the lifestyle changes, and any other criteria. For example, if system 110 would recommend that an individual perform five lifestyle changes to achieve less than a 10% risk improvement, system 110 may communicate to the individual using a low cost communication, such as a letter or e-mail. System 110 may communicate with individuals who can make four lifestyle changes to achieve a 10%-25% risk improvement using a nurse bank that telephones the individuals. If an individual can achieve a risk improvement between 25-50% using three lifestyle changes, system 110 may use both the nurse bank and notify the individual's personal physician for follow-up care; and if an individual can achieve a risk improvement of greater than 50% using two lifestyle changes, a corporate physician or other physician of system 110 may contact the individual personally or visit the individual at work or home. Although these exemplary risk improvement ranges and number of lifestyle interventions have been described, any other combination of lifestyle changes and risk improvements may be used to prioritize communication of health risks to individuals. Moreover, the amount and type of follow-up care that an individual receives may be based on risk improvement and lifestyle changes.

Figure 3:
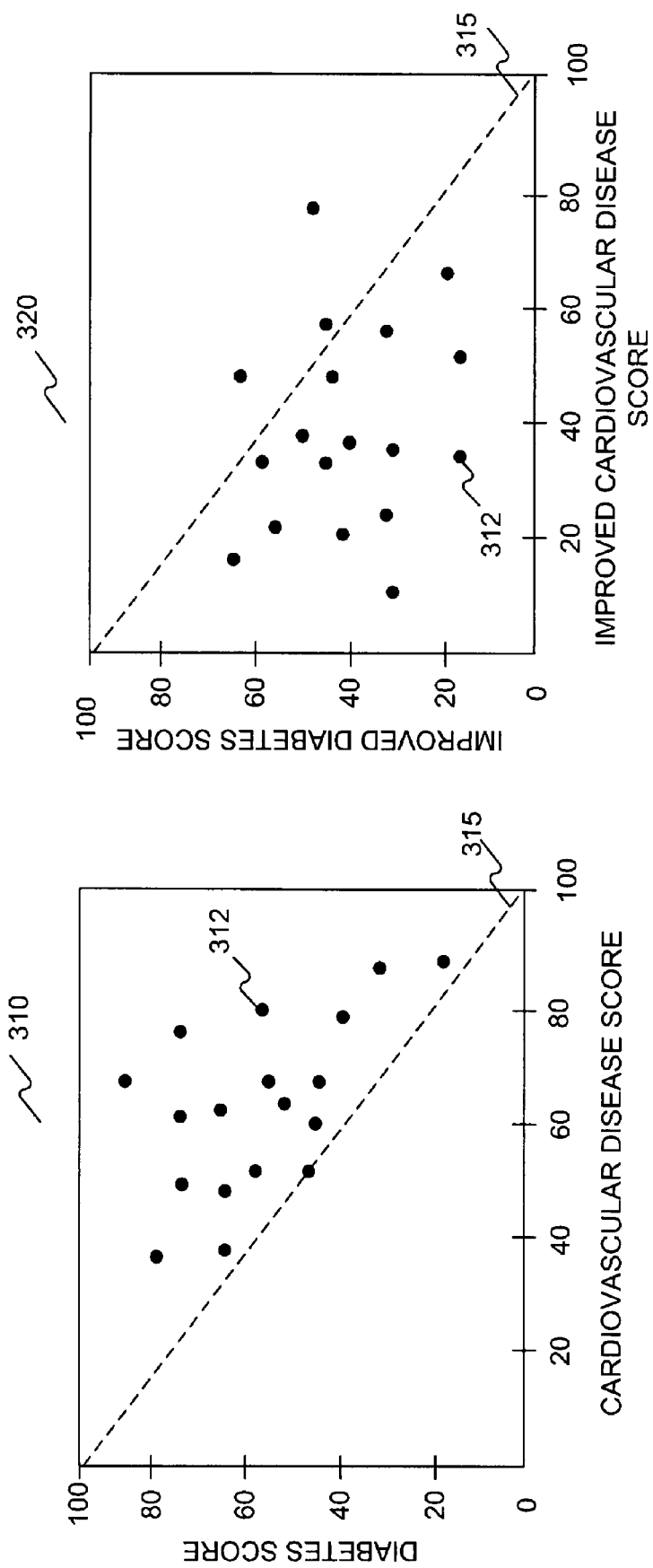
FIG. 3 is a schematic illustration of exemplary graphed health risks.

FIG. 3 is a schematic illustration of exemplary graphed health risks. Graph 310 illustrates a subset of risks for individuals contracting diabetes (y axis) and cardiovascular disease (x axis). Line 315 indicates the cut-off point for including individuals in the subset. Each of the dots 312 represent an individual's scaled health risk for diabetes and cardiovascular disease (as calculated in Step 220). For example, labeled dot 312 indicates an individual with a scaled risk of contracting diabetes of approximately 57 and a scaled risk of contracting cardiovascular disease of approximately 80.

Graph 320 indicates an improved diabetes score and an improved cardiovascular disease score for the subset of individuals. The improved scores demonstrate the amount of improvement that may be obtained for each individual if the individual performs all of the recommended lifestyle changes. As illustrated, the majority of the individuals can reduce their risk of contracting each disease below cut-off point 315 for inclusion in the subset of individuals with higher risk. Individuals who can achieve a large reduction in their risk by making lifestyle changes may receive more personalized communication, whereas individuals who can achieve relatively little reduction in risk may receive little or no communication.

The system may be designed for medical reasons to identify and predict people who are likely to be diagnosed with one or more diseases, allowing preventative treatments or corrective actions to occur prior to disease onset. Risks may be identified and forecasted for any period in the future that adequately identifies a health risk. Individuals may receive targeted communications based on their risk of contracting one or more diseases. By identifying and contacting individuals about their risk for disease, individuals can make lifestyle changes and receive preventative treatments that may delay or eliminate their risk for contracting the disease. Further, although lifestyle interventions have been described, system 110 may also utilize other preventative treatments, such as drugs or surgery, to reduce the risk of contracting one or more diseases.

It will be apparent to those skilled in the art that various modifications and variations may be made to the disclosed methods. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A computer-implemented method for prioritizing communication of a health risk, comprising:
    obtaining, by a processor associated with the computer, health information for individuals;
    determining, by the processor and based on the health information, an initial health risk of each individual contracting each of plurality of diseases;
    calculating, by the processor and based on the initial health risks, an average health risk of each individual contracting the diseases;
    selecting, by the processor, a subset of the individuals based on the average health risks;
    calculating, by the processor, an improved health risk for the subset of the individuals contracting the diseases based on the subset of individuals making lifestyle changes;

calculating, by the processor, a risk improvement for the individuals in the subset based on the average health risk and on the improved health risk;

selecting, by the processor, among a plurality of methods of contacting individuals in the subset, a desired method of contacting individuals in the subset to communicate health risks and lifestyle changes based on a value of the calculated risk improvement; and initiating contacting the individuals in the subset to communicate the health risks and lifestyle changes according to the selected method of contacting.

2. The method of claim 1, further including:

creating, by the processor, a list of the average health risks; and sorting, by the processor, the list such that individuals having higher average health risk are at the top of the list.

3. The method of claim 2, wherein selecting the subset includes selecting a number of the higher risk individuals from the list.

4. The method of claim 1, wherein selecting the subset includes selecting based on a number of lifestyle changes necessary to achieve a defined reduction in the average health risk.

5. The method of claim 1, further including dividing, by the processor, the subset of individuals into groups based on the amount of the risk improvement.

6. The method of claim 1, wherein selecting the method of contacting the individuals in the subset includes selecting based further on a ratio of the value of the risk improvement to a number of the lifestyle changes.

7. The method of claim 1, wherein the selected method of contacting is selected from at least one of: mailing a letter to the individuals in the subset, sending an e-mail to the individuals in the subset, telephoning the individuals in the subset using a nurse bank, notifying a physician for follow-up care of the individuals in the subset, and directly contacting the individuals in the subset by a physician.

8. A non-transitory computer-readable medium comprising program instructions which, when executed by a processor, perform a method for prioritizing communication of a health risk, the method comprising:

obtaining health information for individuals;

determining, based on the health information, an initial health risk of each individual contracting each of a plurality of diseases;

calculating, based on the initial health risks, an average health risk of each individual contracting the diseases;

selecting a subset of the individuals based on the average health risks;

calculating an improved health risk for the subset of the individuals contracting the diseases based on the subset of individuals implementing lifestyle changes;

calculating a risk improvement for the individuals in the subset based on the average health risk and on the improved health risk;

selecting, among a plurality of methods of contacting individuals in the subset, a desired method of contacting individuals in the subset to communicate health risks and lifestyle changes based on a value of the calculated risk improvement; and triggering contacting the individuals in the subset to communicate the health risks and lifestyle changes according to the selected method of contacting.

9. The computer-readable medium of claim 8, wherein the method further includes:

creating a list of the average health risks; and sorting the list with individuals having higher average health risk at the top of the list.

10. The computer-readable medium of claim 9, wherein selecting the subset includes selecting a number of the higher risk individuals from the list.

11. The computer-readable medium of claim 8, wherein selecting the subset includes selecting based on a number of lifestyle changes necessary to achieve a defined reduction in the average health risk.

12. The computer-readable medium of claim 8, wherein the method further includes dividing the subset of individuals into groups based on the amount of risk improvement.

13. The computer-readable medium of claim 8, wherein selecting method of contacting the individuals in the subset includes selecting based on a ratio of the value of the risk improvement to a number of the lifestyle changes.

14. The computer-readable medium of claim 8, wherein the selected method of contacting is selected from at least one of: mailing a letter to the individuals in the subset, sending an e-mail to the individuals in the subset, telephoning the individuals in the subset using a nurse bank, notifying a physician for follow-up care of the individuals in the subset, or directly contacting the individuals in the subset by a physician.

15. A system for prioritizing communication of a health risk, comprising:

a memory;

at least one input device; and at least one central processing unit in communication with the memory and the at least one input device, wherein the central processing unit:

obtains health information for individuals;

determines, based on the health information, an initial health risk of each individual contracting each of plurality of diseases;

calculates, based on the initial health risks, an average health risk of each individual contracting the diseases;

selects a subset of the individuals based on the average health risks;

calculates an improved health risk for the subset of the individuals contracting the diseases based on the subset of individuals implementing lifestyle changes;

calculates a risk improvement for the subset of individuals based on the average health risk and on the improved health risk; and selects, among a plurality of methods of contacting individuals in the subset a desired method of contacting individuals in the subset to communicate health risks and the lifestyle changes based on a value of the calculated risk improvement; and triggering contacting the individuals in the subset to communicate the health risks and lifestyle changes according to the selected method of contacting.

16. The system of claim 15, wherein the central processing unit further:

creates a list of the average health risks; and sorts the list with individuals having higher average health risk at the top of the list.

17. The system of claim 15, wherein selecting the subset includes selecting based on a number of lifestyle changes necessary to achieve a defined reduction in the average health risk.

18. The system of claim 15, wherein the central processing unit further:

selects the method of contacting the based further on a ratio of the value of the risk improvement to a number of the lifestyle changes.

19. The system of claim 15, wherein the central processing unit further:
  divides the subset of individuals into groups based on the amount of the risk improvement, each group having a defined number of individuals; and
  selects the group having the greatest amount of risk improvement.

20. The system of claim 15, wherein the central processing unit is configured to select the method of contacting from at least one of: mailing a letter to the individuals in the subset, sending an e-mail to the individuals in the subset, telephoning the individuals in the subset using a nurse bank, notifying a physician for follow-up care of the individuals in the subset, or directly contacting the individuals in the subset by a physician.

* * * * *